United States Patent [19]

Reed et al.

[11] Patent Number: 5,321,719
[45] Date of Patent: Jun. 14, 1994

[54] THERMOGRAVIMETRIC APPARATUS

[75] Inventors: Kevin J. Reed, Landenberg; Michael J. Levchak, Downingtown, both of Pa.; John W. Schaefer, Wilmington, Del.

[73] Assignee: TA Instruments, Inc., New Castle, Del.

[21] Appl. No.: 67,355

[22] Filed: May 26, 1993

[51] Int. Cl.$^5$ .................. G01N 25/00; G01K 1/14
[52] U.S. Cl. ........................ 374/14; 374/12; 374/10; 374/31; 374/208
[58] Field of Search .............. 374/14, 10, 12, 157, 374/208, 31

[56] References Cited

U.S. PATENT DOCUMENTS

| | | | |
|---|---|---|---|
| 3,271,996 | 9/1966 | Paulik et al. | 374/14 |
| 3,303,689 | 2/1967 | Paulik et al. | 374/12 |
| 3,344,654 | 10/1967 | Erdey et al. | |
| 3,373,598 | 3/1968 | Johnson et al. | 374/14 |
| 3,469,455 | 9/1969 | Iwata | 374/14 |
| 3,712,110 | 1/1973 | Paulik et al. | |
| 3,902,354 | 9/1975 | Harlan et al. | |
| 4,606,649 | 8/1986 | Mikhail | 374/14 |
| 4,762,428 | 8/1988 | Villiger | 374/14 |
| 4,763,536 | 8/1988 | Beshoory | 374/14 |
| 4,838,706 | 6/1989 | Coey et al. | 374/54 |
| 5,147,137 | 9/1992 | Thiesen | 374/208 |

FOREIGN PATENT DOCUMENTS

| | | | |
|---|---|---|---|
| 0033961 | 8/1981 | European Pat. Off. | 374/12 |
| 2139494 | 1/1973 | France . | |
| 62-4654 | 1/1987 | Japan . | |
| 1324982 | 7/1973 | United Kingdom | 374/10 |
| 1388952 | 4/1975 | United Kingdom | 374/12 |
| 02856 | 4/1988 | World Int. Prop. O. . | |

OTHER PUBLICATIONS

Groot, C. et al., "Automatic Recording Thermobalance," Analytical Chemistry, vol. 29, No. 5 (May 1957).
Breusov, O. et al., "An apparatus for automatic thermogravimetry," Industrial Laboratory, vol. 39, No. 10, p. 1669 Oct. 1973 (published Apr. 1974).
F. Paulik et al., "Thermoanalytical Examination Under Quasi-Isothermal, Quasi-Isobaric Conditions," Thermochimica Acta, vol. 100, pp. 23-26 (1986).
G. M. Lukaszewski, "Accuracy in Thermogrvimetric Analysis", Nature, vol. 194, No. 4832, pp. 959-961 (Jun. 1962).
J. Paulik, F. Paulik, "'Quasi-isothermal' thermogravimetry", Anal. Chim. Acta, vol. 56, pp. 328-331 (1971).
F. Paulik, J. Paulik, M. Arnold and R. Naumann, "Investigation on the Thermal Behaviour of $Mg(NO_3)26-H_2O$ I. the Decomposition Behaviour", J. Ther. Anal., vol. 34, pp. 627-635 (1988).
J. Paulik, F. Paulik and M. Arnold, "The Derivatograph-C. A microcomputer-controlled simultaneous TG, DTG, DTA, TD and EGA apparatus I", J. Therm. Anal., vol. 32, pp. 301-309 (1987).
J. Rouquerol, "Method d'analyse thermique sous faible pression et a vitesse de composition constante", Memoires Presentees a la Societe Chimique (Oct. 1963).
J. Chiu, "Applications of Thermogravimetry to the Study of High Polymers", Applied Polymer Symposia, No. 2, pp. 25-43 (1966).

Primary Examiner—Diego F. F. Gutierrez
Attorney, Agent, or Firm—Kirkland & Ellis

[57] ABSTRACT

The present invention is a thermogravimetric instrument having a ceramic sample support and a ceramic balance beam. The ceramic platform is rigidly attached to the hot end of the ceramic balance beam. An inert metal liner is press fitted into the ceramic sample platform. In a preferred embodiment, a thermocouple is directly attached to the inert metal liner. The thermocouple wires are routed through the length of the ceramic balance beam and are attached to the cold end of the ceramic balance beam with adhesive. The inert metal liner could be fabricated from platinum or from platinum alloys.

34 Claims, 3 Drawing Sheets

THERMOGRAVIMETRIC APPARATUS

BACKGROUND

Field of the Invention

The present invention relates to thermogravimetric techniques for determining the composition, phase, structure or other properties of a sample of material.

Thermogravimetric Analysis ("TGA") techniques generally comprise measuring the weight change of a material as a function of temperature, or as a function of time at a controlled temperature. The sample temperature is strictly controlled throughout the analysis. The classic TGA method comprises heating the sample at a constant heating rate, e.g., at 10° C. to 50° C. per minute, while the weight change or the percent of weight change of the sample is recorded versus temperature. Whenever the sample undergoes a chemical or physical transformation that affects the weight of the sample, the change in weight may be interpreted to analyze the composition, structure, or thermal stability of the sample.

There are two general types of TGA instruments: vertical TGA instruments and horizontal TGA instruments. Vertical TGA instruments support the sample/reference holders vertically. Horizontal TGA systems support the sample/reference holders at the end of a horizontal beam. The present invention applies to horizontal TGA instruments.

TGA instruments can utilize either direct or indirect temperature measurement. Direct temperature measurement designs have the temperature sensor in physical contact with either the sample or the sample holder. The sensor is in physical contact with the sample or the sample holder when there exists a low thermal resistance path between the sensor and the sample or the sample holder. Indirect temperature measurement designs have the temperature measuring sensor separated from the sample and the sample holder by the atmosphere which surrounds the sample. Each type of temperature measurement has advantages. The main advantage of indirect temperature measurement lies in the reduced complexity of the balance beam and temperature measuring apparatus. The main advantage of direct temperature measurement lies in the increased accuracy of the temperature measurement because thermal gradients between the sample and the sensor are significantly reduced.

Differential Thermogravimetric Analysis ("DTGA") instruments measure the weight change of a sample of the material with reference to the weight change of a reference material, as a function of the temperature of the sample, or as a function of time at a controlled temperature. DTGA instruments compensate for the effects of heating rate and ambient conditions that could cause changes in the measured weight of the sample and reference. The DTGA technique can increase the sensitivity of the measurement of the change in sample weight by removing large offsets in the value of the sample weight whenever the precision of the measuring apparatus is limited.

Differential Scanning Calorimetry ("DSC") is a thermal analysis technique which measures the temperatures and heat flow associated with transitions in materials as a function of time and temperature. These measurements provide quantitative and qualitative information about the sample transitions that involve endothermic or exothermic processes, or changes in heat capacity.

Differential Thermal Analysis ("DTA"), like DSC, measures the temperatures and heat flow associated with transitions in materials as a function of time and temperature. However, unlike DSC, DTA results are semi-quantitative. DTA is generally carried out at higher temperatures than DSC.

Simultaneous TGA/DTA and simultaneous TGA/DSC, measure weight change and differential temperature changes simultaneously in a sample and a reference, as a function of temperature, or as a function of time at a controlled temperature. Simultaneous measurement of these two physical properties improves productivity of the measurement and simplifies interpretation of the results. The complementary information obtained from the simultaneous measurement allows differentiation between events which have no associated weight change (e.g. melting and crystallization), and those which involve a weight change (e.g. degradation and evaporation).

The simultaneous measurement of weight changes and differential temperature changes on the same sample also assures identical experimental conditions and data sampling for both measurements, thereby eliminating those sources of uncertainty.

Differential temperature measurements generally require the use of a direct temperature measurement design because the differential temperatures being measured are typically not greater than the thermal gradients which occur with indirect temperature measurements.

Conventional horizontal simultaneous TGA/DTA, and simultaneous TGA/DSC instruments are generally constructed with either one or two support beams. The beam(s) extend from the balance pivot point, which is located outside the TGA furnace, to the sample support point, which is located inside the furnace. Single-beam simultaneous designs have two support positions at the end of the beam. The temperature at each support position can be measured independently. The temperature measurements can be combined for DTA or DSC measurements.

Two-beam designs provide for differential temperature and weight measurements. The sample beam provides the sample temperature and weight measurements and the reference beam provides the reference temperature and weight measurements for DTA/DTGA or DSC/DTGA analysis.

Alternate designs for horizontal simultaneous DTA/TGA and DSC/TGA instruments utilize multiple beams, some of which are attached to balance mechanisms and some of which are fixed to rigid mounts outside the furnace. For example, a three beam design uses two rigid mount beams, each with a sample platform, to measure the differential temperature of a sample and a reference. The third beam simultaneously measures the weight change of another sample of the same material. Many different design configurations are possible, including designs with and without temperature measurement at the end of the beam, and with and without balance mechanisms attached to the beams.

The accuracy of weight change measurements in conventional horizontal TGA instruments is reduced by the problem of beam growth. The term "beam growth" refers to the dimensional change of the balance beam due to thermal expansion of the beam as the sample and beam are heated in the TGA furnace. If the dimensional change in the TGA beam moves the sample further away from the pivot point of the horizontal balance, then an apparent increase in sample weight will be recorded. Conversely, any movement of the sample toward the pivot point, typically caused by cooling of the beam, will result in an apparent decrease in sample weight. Normally a correction is applied to the TGA weight change measurement to compensate for beam growth. In conventional horizontal TGA designs the correction is often complex and inaccurate due to the simultaneous thermal expansion of two or more dissimilar materials in the balance beam/support assembly. The accuracy of the correction is further reduced when the sample support materials are not rigidly fixed with respect to each other, and with respect to the balance pivot point.

The accuracy of the weight change measurement in conventional horizontal design TGA instruments is also affected by the accuracy and reproducibility of the sample placement. The sample is usually placed in a removable holder which is then placed on, or suspended from, a sample support at the end of the TGA balance beam. Any variation in the distance between the balance pivot point and the sample will cause an error in the weight measurement. In indirect temperature measurement designs the sample holder is typically suspended by a bail wire from the support. In direct temperature measurement designs the sample holder typically sits on a temperature measurement platform or bead. Any movement in the platform or bead due to mishandling, heat annealing, or thermal expansion will adversely affect the accuracy of the temperature measurement.

Conventional horizontal simultaneous TGA/DTA instruments are constructed with a platinum liner that acts as a sample support platform. This liner is welded to a thermocouple bead. The thermocouple wires are routed through the interior of a hollow balance beam to exit at the cold end of the beam, near the balance pivot. This construction has two principal disadvantages. First, the sample holder is held in position only by the thermocouple wires. This is not a very secure construction, and after several runs to high temperatures the thermocouple wires become soft and malleable, allowing the sample holder to move. Furthermore, the act of loading a sample holder can move the thermocouple wires, and therefore, the sample holder. Any movement of the sample holder adversely affects the sample weight measurement, because it results in a change in the distance between the pivot point of the balance and the sample. Second, the platinum liner itself tends to become soft and to lose its shape after several runs. This also adversely affects the consistency and reproducibility of the temperature measurement.

SUMMARY OF THE INVENTION

The present invention is an improved sample support and balance beam apparatus for horizontal TGA instruments comprising a ceramic beam with a ceramic sample support platform rigidly attached to the end of the beam, an inert metal liner press fitted into the support platform, with rigid attachment of the thermocouple wires at the cold end of the beam. During a TGA run, the end of the beam with the support platform attached (the "hot end of the beam") is placed in a controlled atmosphere inside the TGA furnace. The opposite end of the beam (the "cold end of the beam") is attached to the TGA balance mechanism which is typically a taut band meter movement.

Thermocouple wires are attached to the inert metal liner to provide a means for direct and accurate measurement of the temperature of the sample and/or reference holder. The thermocouple wires lead from the metal liner, through the ceramic beam, and out the cold end of the beam where they are rigidly adhered to the end of the beam with adhesive, or other suitable attaching means. Alternatively, the wires may be supported along the outside of the beam or wrapped around the outside of the beam instead of passing through the inside of the beam. The beam may have a circular, rectangular, I-beam or other cross-section, as long as it provides adequate stiffness and support for the sample.

The sample and/or reference platforms and the inert metal liners are rigidly attached to the ceramic beam. This rigid attachment constrains the liners to remain at the same position run after run with respect to the ceramic beams. The weight measurements thus obtained are therefore highly reproducible, allowing for the use of calibration techniques to improve the accuracy of the weight measurements, and allowing for easier and more accurate correction for effects such as beam growth. Furthermore, in simultaneous TGA/DTA or simultaneous TGA/DSC, the use of this rigid assembly improves the reproducibility of the DTA/DSC measurements. The rigid support for the inert metal liner also prevents the liner from losing its shape when it becomes soft and malleable after several runs at high temperature. This makes it easier to load and unload sample and/or reference holders.

Because the liner has a very close press fit with the ceramic platform, and the sample and/or reference holder has a very close fit with the liner, the holder is constrained so that it cannot move around in the liner, which increases the reproducibility and accuracy of the weight and temperature measurements.

The ceramic beams are fabricated with multiple bores to accommodate and separate the thermocouple wires, and to reduce beam weight while maintaining beam stiffness. The beams are preferably fabricated with at least three bores. Three-bore beams provide greater stiffness with reduced weight, compared to conventional two-bore beams. Alternatively, the beam may have only a single bore through which all of the thermocouple wires pass (with electrical insulation to prevent short circuits between the thermocouple wires).

The thermocouple wires exiting the ceramic beams at the cold end of the beam are encapsulated with an adhesive to rigidly attach the thermocouple wires to the end of the beam. This attachment eliminates noise in the TGA weight measurement caused by differential thermal expansion between the wires and the beam. Without the adhesive, the thermocouple wires try to grow in length but are restrained by friction within the ceramic bores. When sufficient expansion force builds up to overcome the friction with the bores, the thermocouple wires move abruptly which produces a shift in the TGA weight measurement. Such shifts reduce the accuracy of the TGA weight measurement and contribute anomalies to the recorded weight loss versus temperature/time data of the instrument. Depending upon the frequency and amplitude of these anomalies, they may be interpreted as artifacts or seen as noise in the data, thus reducing both the accuracy and the sensitivity of the instrument. The abrupt movement of the thermocouple wires can also shift the position of the thermocouple with respect to the sample or reference holder, which also reduces the accuracy and sensitivity of the temperature measurement.

A first object of the present invention is to improve the reproducibility and accuracy of TGA weight and temperature measurements.

A second object of the present invention is to improve the reproducibility and accuracy of simultaneous TGA/DTA and TGA/DSC differential temperature measurements.

A third object of the present invention is to simplify TGA weight corrections which seek to compensate for the effects of thermal expansion.

A fourth object of the present invention is to reduce adverse effect that may result from the process of loading and unloading sample and reference materials.

A fifth object of the present invention is to simplify and improve TGA instrument setup and calibration.

DESCRIPTION OF THE PREFERRED EMBODIMENT OF THE INVENTION

The following detailed description of the preferred embodiment of the present invention applies specifically to a horizontal TGA apparatus in which the sample support beam is attached to a balance mechanism. However, it should be understood that the present invention could be used with any furnace/measurement system in which a rigid beam supports a sample (or sample holder), in a furnace such that the hot end of the beam extends into the furnace, the cold end of the beam is attached outside the furnace, and the temperature of the sample is directly measured at the hot end of the beam. This includes Differential Thermal Analysis and Differential Scanning Calorimetry.

Figure 1:
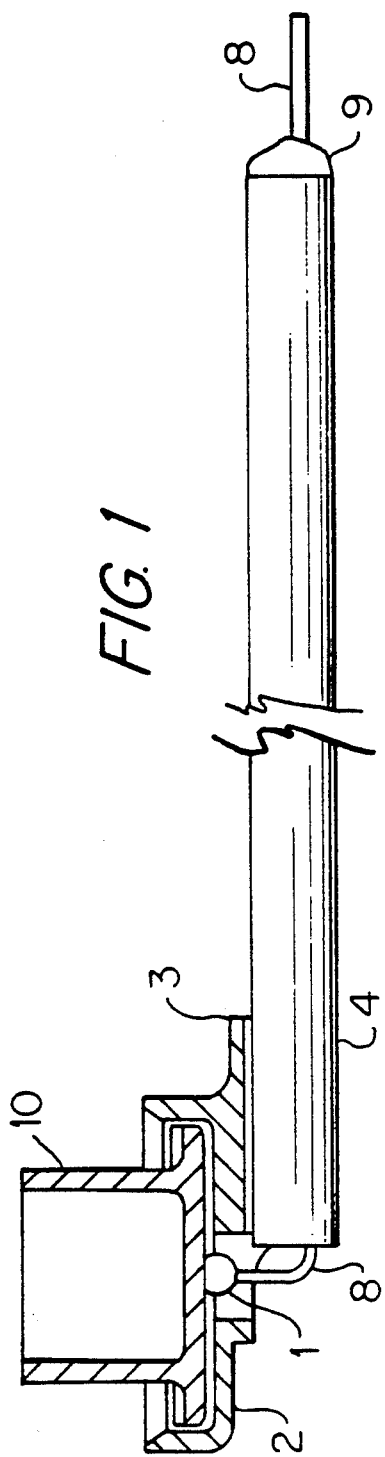
FIG. 1 is a schematic diagram of the sample beam assembly.
Figure 4A:
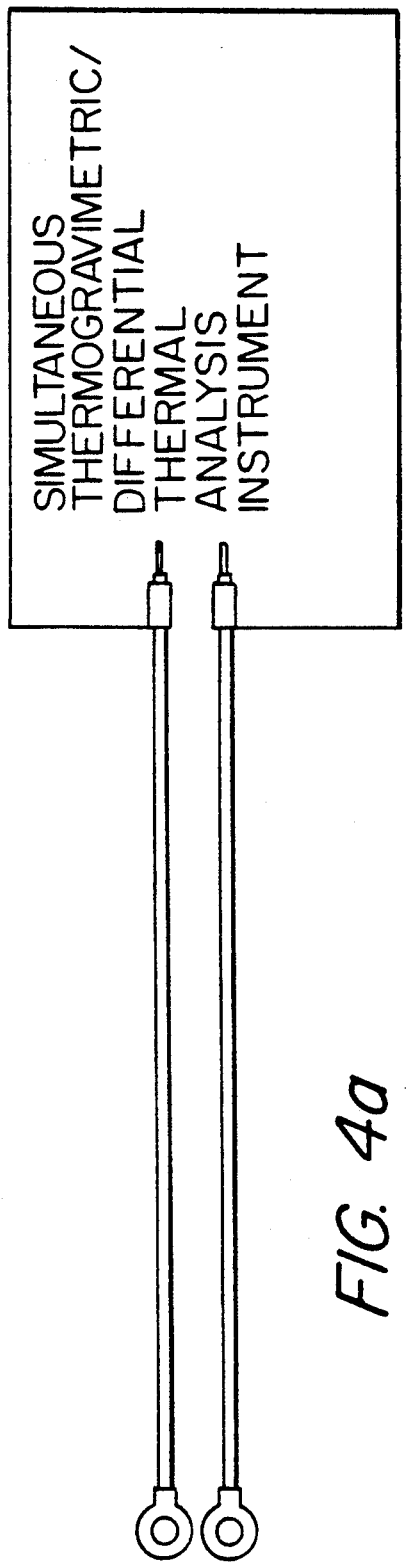
FIG. 4a is a schematic diagram of a dual beam simultaneous thermogravimetric/differential thermal analysis instrument.
Figure 4B:
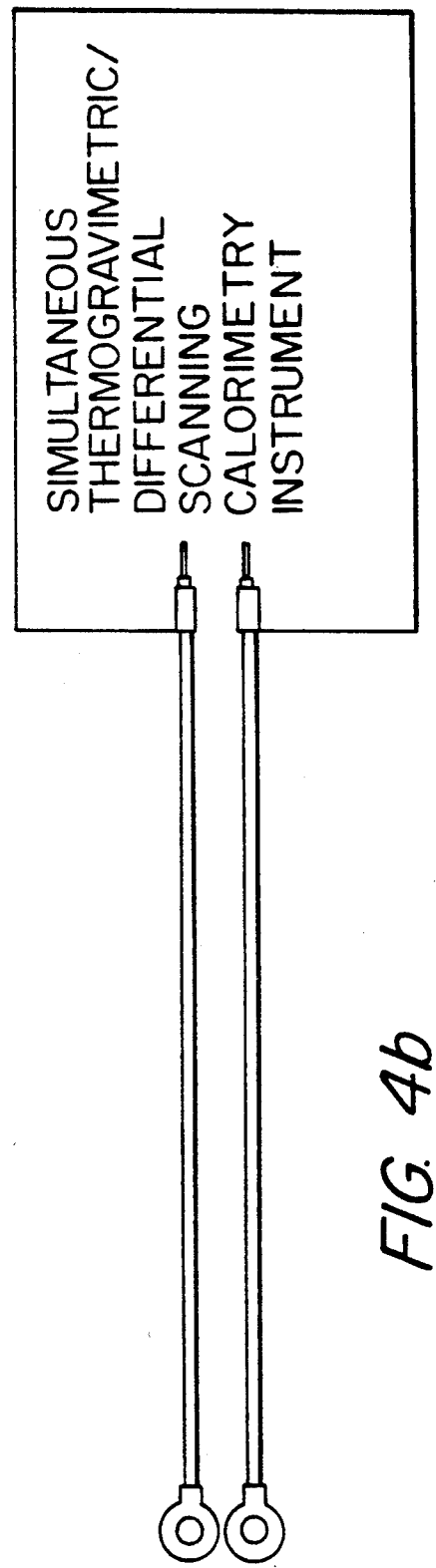
FIG. 4b is a schematic diagram of a dual beam simultaneous thermogravimetric/differential scanning calorimetry instrument.

FIG. 1 is a schematic diagram of the preferred embodiment of the present invention. The ceramic beam assembly shown in FIG. 1 is an arm of a TGA horizontal balance, and carries a thermocouple wire assembly. For DTGA, simultaneous TGA/DTA, or simultaneous TGA/DSC instruments, the beam assembly shown in FIG. 1 would be one of a pair of sample and reference beam assemblies used for differential measurements (as shown in FIGS. 4a and 4b).

As shown in FIG. 1, the beam assembly comprises a type R thermocouple bead 1 welded to the bottom of platinum liner 2 which is press fitted into ceramic platform 3 which is cemented to a three-bore ceramic beam 4. Sample holder 10 rests in the bottom of platinum liner 2 which conducts heat from holder 10 to thermocouple bead 1. Note that the ceramic beam assembly shown in FIG. 1 is a direct temperature measurement design because the thermocouple bead is in direct physical contact with the platinum liner which is in direct physical contact with the sample holder. At present, alumina is being used as the ceramic for ceramic platform 3 and ceramic beam 4. Other suitable ceramic materials may include sapphire, quartz, fused silica, silicon carbide, silicon nitride or zirconia.

Figure 2:
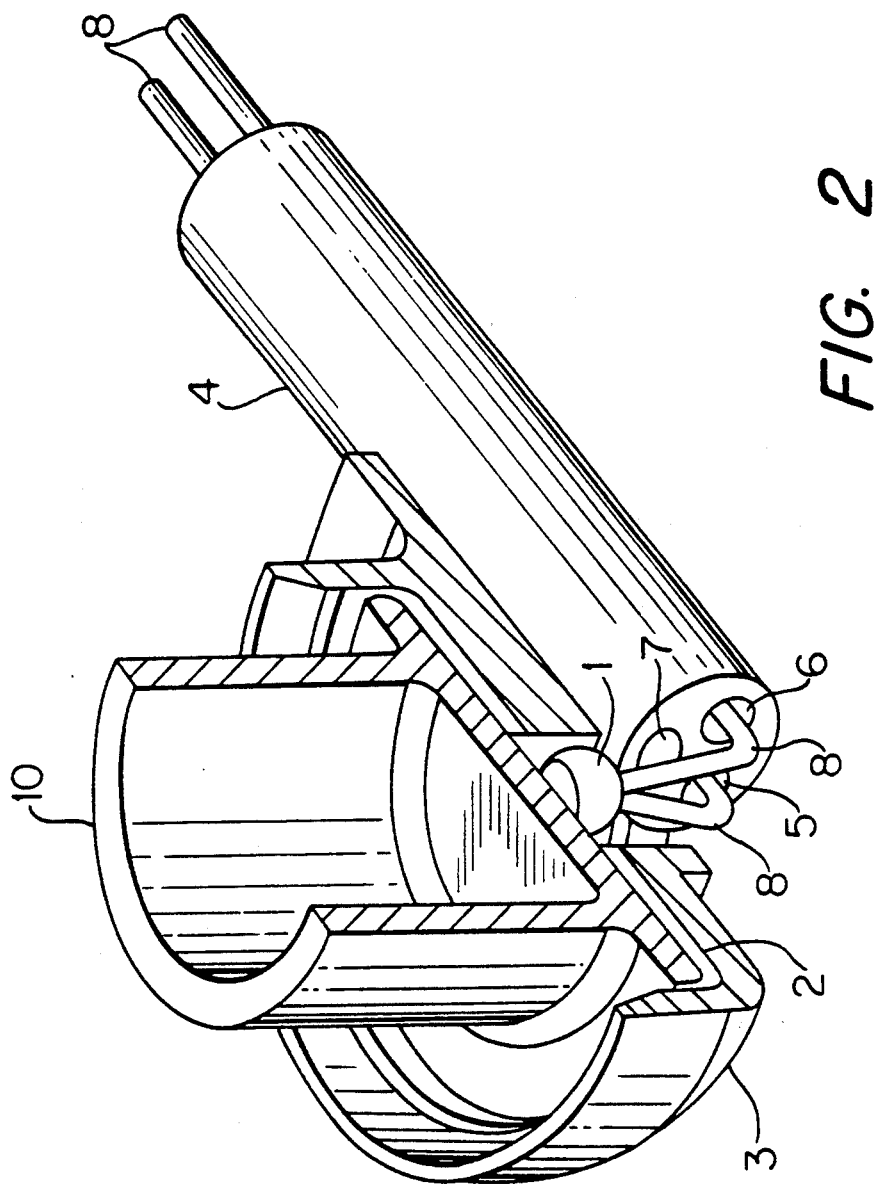
FIG. 2 is a perspective view of the sample platform/beam assembly.

As shown in FIG. 2, the type R thermocouple wires 8 start at the thermocouple bead 1 and enter ceramic beam 4 just below the ceramic platform 3 passing through bores 5 and 6. Bore 7 remains empty. As shown in FIG. 1, thermocouple wires 8 exit bores 5 and 6 at the opposite end of beam 4, where they are encapsulated with adhesive 9 which prevents movement of the thermocouple wires.

The inert metal liner is preferably fabricated from platinum or platinum alloys, e.g., platinum alloys containing rhodium, or iridium, or both rhodium and iridium. Gold and gold alloys may also prove to be suitable materials for inert liners.

Figure 3:
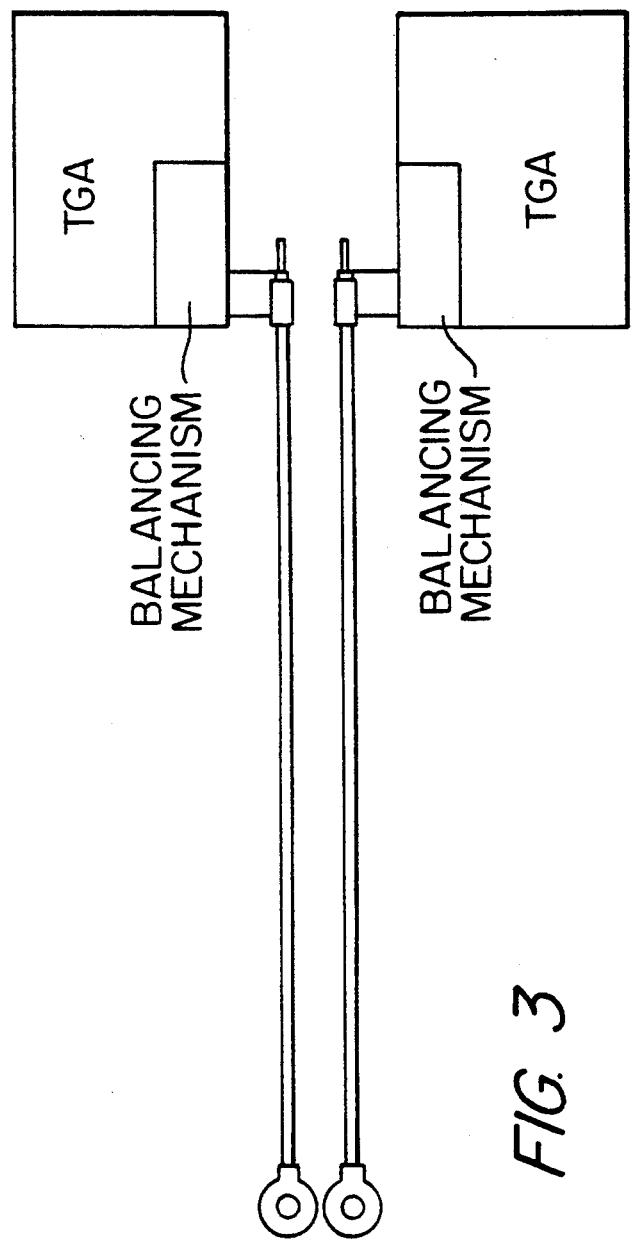
FIG. 3 is a top view of a dual beam thermogravimetric instrument.

FIG. 3 is a top view of a dual beam thermogravimetric instrument. FIG. 4a is a schematic diagram of a dual beam simultaneous thermogravimetric/differential thermal analysis instrument. FIG. 4b is a schematic diagram of a dual beam simultaneous thermogravimetric/differential scanning calorimetry instrument.

The foregoing disclosure of a preferred embodiment of the present invention has been presented for purposes of illustration and description. It is not intended to be exhaustive or to limit the invention to the precise forms disclosed. Many variations and modifications of the embodiment described herein will be obvious to one of ordinary skill in the art in light of the above disclosure. For example, the ceramic sample support platform and the ceramic balance beam may be fabricated as one piece, instead of being fabricated separately and then attaching the ceramic sample support platform to the ceramic beam. The scope of the invention is to be defined only by the claims appended hereto, and by their equivalents.

What is claimed is:

1. A beam system for a horizontal thermogravimetric analysis instrument comprising:
    (a) a first ceramic balance beam having a hot end and a cold end;
    (b) a first ceramic sample support platform rigidly attached to the hot end of the first ceramic balance beam;
    (c) a first inert metal liner rigidly attached to the first sample support platform, said first inert metal liner having a bottom surface; and
    (d) a thermocouple having a thermocouple bead attached to the bottom surface of the first metal liner.

2. The beam system of claim 1, wherein the first ceramic balance beam has at least one bore, and wherein said thermocouple is comprised of thermocouple wires routed through the said at least one bore from the hot end of the first ceramic balance beam to the cold end of the first ceramic balance beam.

3. The beam system of claim 2, wherein the thermocouple wires are attached to the first ceramic balance beam at the cold end of the first ceramic balance beam.

4. The beam system of claim 3 wherein the thermocouple wires are adhesively attached to the cold end of the first ceramic balance beam.

5. The beam system of claim 2, wherein the first ceramic balance beam has at least two bores, and each thermocouple wire is routed separately through one bore.

6. The beam system of claim 5, wherein the first ceramic balance beam has at least three bores, and at least one bore does not have a thermocouple wire routed through it.

7. The beam system of claim 1, further comprising a second ceramic balance beam, said second ceramic balance beam comprising a hot end and a cold end, a second ceramic support platform rigidly attached to the hot end of the second ceramic balance beam, a second inert metal liner rigidly attached to the second ceramic support platform, and a thermocouple bead attached to the second inert metal liner.

8. The beam system of claim 1, wherein the first inert metal liner is a platinum metal liner.

9. The beam system of claim 1, wherein the inert first metal liner is a platinum alloy metal liner, said alloy containing rhodium and iridium.

10. The beam system of claim 1, wherein the first inert metal liner is press fitted into the first ceramic support platform.

11. A horizontal thermogravimetric analysis instrument comprising:
(a) a first ceramic balance beam having a hot end and a cold end connected to a means for measuring weight change;
(b) a first ceramic sample support platform rigidly attached to the hot end of the first ceramic balance beam;
(c) a first inert metal liner rigidly attached to the first ceramic sample support platform, said first inert metal liner having a bottom surface; and
(d) a temperature sensor attached in direct physical contact with the first inert metal liner.

12. The thermogravimetric analysis instrument of claim 11, further comprising a second ceramic balance beam, said second ceramic balance beam comprising a hot end and a cold end, a second ceramic support platform rigidly attached to the hot end of the second ceramic balance beam, a second inert metal liner rigidly attached to the second ceramic support platform, and a thermocouple bead attached to the second inert metal liner.

13. The thermogravimetric instrument of claim 11, wherein the thermogravimetric instrument is a simultaneous thermogravimetric analysis/differential thermal analysis instrument.

14. The thermogravimetric instrument of claim 11, wherein the thermogravimetric instrument is a simultaneous thermogravimetric analysis/differential scanning calorimeter.

15. The thermogravimetric instrument of claim 11, wherein the first inert metal liner is a platinum metal liner.

16. The thermogravimetric instrument of claim 11, wherein the first inert metal liner is a platinum alloy metal liner containing rhodium and iridium.

17. The thermogravimetric instrument of claim 11, wherein the first inert metal liner is press fitted into the first ceramic support platform.

18. A thermal analysis instrument comprising:
(a) a first ceramic balance beam having a first ceramic sample support platform at a first end of the first ceramic balance beam and a means for measuring weight change connected to a second end of the first ceramic balance beam;
(b) a first inert metal liner rigidly attached to the first ceramic sample support platform, said first inert metal liner having a bottom surface; and
(c) a temperature sensor attached in direct physical contact with the first inert metal liner.

19. The thermal analysis instrument of claim 18, wherein the temperature sensor is a thermocouple comprised of thermocouple wires, wherein the first ceramic balance beam has at least one bore, and wherein said thermocouple wires are routed through the said at least one bore from the first end of the first ceramic balance beam to a second end of the first ceramic balance beam.

20. The thermal analysis instrument of claim 19, wherein the thermocouple wires are attached to the first ceramic balance beam at the second end of the first ceramic balance beam.

21. The thermal analysis instrument of claim 18, wherein the instrument is a differential thermogravimetric instrument, further comprising a second ceramic balance beam, said second ceramic balance beam comprising a second ceramic sample support platform at a first end of the second ceramic balance beam, a means for measuring weight change connected to a second end of the second ceramic balance beam and a second inert metal liner rigidly attached to the second sample support platform, said second inert metal liner having a bottom surface, and a temperature sensor attached in direct physical contact with the second inert metal liner.

22. The thermal analysis instrument of claim 18, wherein the thermal instrument is a simultaneous thermogravimetric analysis/differential thermal analysis instrument.

23. The thermal analysis instrument of claim 18, wherein the thermal instrument is a simultaneous thermogravimetric analysis/differential scanning calorimeter.

24. The thermal analysis instrument of claim 18, wherein the first inert metal liner is a platinum metal liner.

25. The thermal analysis instrument of claim 18, wherein the first inert metal liner is a platinum alloy metal liner, said alloy containing rhodium and iridium.

26. The thermal analysis instrument of claim 18, wherein the first inert metal liner is press fitted into the first ceramic support platform.

27. A ceramic balance beam system comprising:
(a) a ceramic sample platform at a first end of a ceramic balance beam;
(b) an inert metal liner rigidly attached to the ceramic balance beam; and
(c) a thermocouple, said thermocouple having two thermocouple wires and a thermocouple bead, wherein said thermocouple bead is in direct physical contact with the inert metal liner, and wherein the two thermocouple wires are adhesively attached to a second end of the ceramic balance beam.

28. The ceramic balance beam system of claim 27, wherein the inert metal liner is press fitted into the ceramic sample platform.

29. The ceramic balance beam system of claim 27, wherein the inert metal liner is a platinum metal liner.

30. The ceramic balance beam system of claim 27, wherein the ceramic balance beam has at least two bores running down the length of the beam, one thermocouple wire is routed through one bore and the other thermocouple wire is routed through another bore, and the thermocouple is a type R thermocouple.

31. The ceramic balance beam system of claim 27, wherein the inert metal liner is a platinum metal alloy, said platinum metal alloy containing rhodium and iridium.

32. The ceramic balance beam system of claim 27, wherein the inert metal liner is a platinum alloy containing rhodium.

33. The ceramic balance beam system of claim 27, wherein the inert metal liner is a platinum alloy containing iridium.

34. The ceramic balance beam system of claim 27, wherein the ceramic sample platform has a hole in its bottom surface, and the thermocouple is positioned in the hole in the bottom surface of the ceramic sample platform.

* * * * *